United States Patent
Yu et al.

(10) Patent No.: US 10,281,435 B2
(45) Date of Patent: May 7, 2019

(54) LIFTING SYSTEM AND ULTRASOUND INSPECTION MACHINE INCORPORATING THE SAME

(71) Applicant: General Electric Company, Schenectady, NY (US)

(72) Inventors: Xun Yu, Shaghai (CN); Zheng Huang, Shanghai (CN)

(73) Assignee: GENERAL ELECTRIC COMPANY, Schenectady, NY (US)

(*) Notice: Subject to any disclaimer, the term of this patent is extended or adjusted under 35 U.S.C. 154(b) by 228 days.

(21) Appl. No.: 15/102,332

(22) PCT Filed: Dec. 12, 2014

(86) PCT No.: PCT/US2014/070004
§ 371 (c)(1),
(2) Date: Jun. 7, 2016

(87) PCT Pub. No.: WO2015/089392
PCT Pub. Date: Jun. 18, 2015

(65) Prior Publication Data
US 2017/0010241 A1      Jan. 12, 2017

(30) Foreign Application Priority Data

Dec. 13, 2013   (CN) .......................... 2013 1 0685202

(51) Int. Cl.
*B66F 3/46* (2006.01)
*G01N 29/22* (2006.01)
(Continued)

(52) U.S. Cl.
CPC .......... *G01N 29/225* (2013.01); *B66B 7/046* (2013.01); *B66B 7/047* (2013.01); *B66B 9/02* (2013.01);
(Continued)

(58) Field of Classification Search
CPC ...... G01N 29/225; B66B 7/046; B66B 7/047; B66B 9/02; B66F 3/02; B66F 3/46
(Continued)

(56) References Cited

U.S. PATENT DOCUMENTS 3,416,364 A    12/1968  Wycherley
5,269,643 A *  12/1993  Kodama ........... H01L 21/67781
                                                          414/331.01
(Continued)

FOREIGN PATENT DOCUMENTS

CN         1492834 A      4/2004
CN       101200272 A      6/2008
(Continued)

OTHER PUBLICATIONS

Unofficial English Translation of Chinese Office Action and Search Report issued in connection with corresponding CN Application No. 201310685202.X dated Nov. 15, 2016.
(Continued)

*Primary Examiner* — Lisa M Caputo
*Assistant Examiner* — Suman K Nath
(74) *Attorney, Agent, or Firm* — GE Global Patent Operation

(57) ABSTRACT

A lifting device, which is configured to lift or drop at least one load bearing mechanism. The lifting device includes a power driving mechanism and multiple lifting mechanisms connecting to the power driving mechanism. The multiple lifting mechanisms march the load bearing mechanism at least from a first height location to a second height location in a rolling manner under a function of a driving force provided by the power driving mechanism. An embodiment of the present invention further discloses an ultrasonic inspection system using the lifting device.

6 Claims, 9 Drawing Sheets

(51) Int. Cl.
*B66B 7/04* (2006.01)
*G01N 29/28* (2006.01)
*B66B 9/02* (2006.01)
*B66F 3/02* (2006.01)

(52) U.S. Cl.
CPC .................. *B66F 3/02* (2013.01); *B66F 3/46* (2013.01); *G01N 29/28* (2013.01)

(58) Field of Classification Search
USPC ............................................. 73/596, 662–669
See application file for complete search history.

(56) References Cited

U.S. PATENT DOCUMENTS

| | | | | |
|---|---|---|---|---|
| 6,668,650 | B1* | 12/2003 | Lafleur | G01M 7/00 73/571 |
| 9,213,017 | B2 | 12/2015 | Yu et al. | |
| 2004/0055831 | A1 | 3/2004 | Huber | |
| 2009/0288918 | A1* | 11/2009 | Schmitt | B66F 7/025 187/216 |
| 2012/0104781 | A1 | 5/2012 | Finck | |
| 2012/0175480 | A1 | 7/2012 | Lee | |

FOREIGN PATENT DOCUMENTS

| | | |
|---|---|---|
| CN | 101778792 | 7/2010 |
| CN | 101806653 A | 8/2010 |
| CN | 102421565 A | 4/2012 |
| CN | 102519870 A | 6/2012 |
| CN | 102640072 A | 8/2012 |
| GB | 2025872 A | 1/1980 |
| WO | 200101103 A1 | 1/2001 |

OTHER PUBLICATIONS

International Search Report and Written Opinion issued in connection with corresponding PCT application PCT/US2014070004 dated Aug. 31, 2015.

* cited by examiner

LIFTING SYSTEM AND ULTRASOUND INSPECTION MACHINE INCORPORATING THE SAME

TECHNICAL FIELD

Embodiments of the present invention relate to a lifting device, and in particular, to an improved lifting device that is applied to the ultrasonic inspection field.

BACKGROUND

In addition to being applied to the medical field for checking a health condition of a specific part of a human body, an ultrasonic inspection technology is further used as a nondestructive testing technology (Non Destructive Testing, NDT) which is widely applied to various industrial fields. The industry has invented various "industrial ultrasonic nondestructive flaw detector" or "industrial ultrasonic detector" that are used to detect "a health condition" of surfaces or interiors of various to-be-detected workpieces or objects, so as to detect whether an internal break or crack occurs in the workpieces. For example, an invention application of the United States field with the application Ser. No. 13/658,841 on Oct. 24, 2012 and entitled "ROTATING ULTRASONIC DETECTING APPARATUS WITH HYDRAULIC LIFT UNIT" discloses an industrial-use ultrasonic inspection system, which is referenced herein.

A typical ultrasonic inspection system includes at least one ultrasonic probe and a workpiece holding apparatus. During inspection performed on a to-be-detected workpiece, the workpiece holding apparatus moves the to-be-detected workpiece to a proper location, starts the ultrasonic probe to transmit an ultrasonic wave to the to-be-detected workpiece, enables the transmitted ultrasonic wave to be conducted, through a liquid acoustic transmission medium (such as water), to the to-be-detected workpiece, receives a return ultrasonic wave that is still conducted to the ultrasonic probe through a liquid acoustic transmission medium after being reflected by the to-be-detected workpiece, and performs a specific image processing algorithm to processes the received return ultrasonic wave, so as to construct an ultrasonic image of the to-be-detected workpiece. The ultrasonic reflected by a break or crack location significantly changes, and therefore the ultrasonic image constructed through observation can determine various defects in the to-be-detected workpiece.

In specific application occasions, a lifting device needs to be designed to flexibly lift or drop to-be-detected workpieces to different heights, so that the ultrasonic probe can be conveniently used to perform ultrasonic inspection on the to-be-detected workpieces. A detect that exists in an existing lifting device is that a shape of a workpiece bearing mechanism changes under a function of weight of the workpiece bearing mechanism, which causes interference (or deadlock) between the workpiece bearing mechanism and a guide pillar, and therefore the to-be-detected workpiece cannot move up and down under a function of a power driving system to perform normal ultrasonic inspection.

BRIEF SUMMARY OF THE INVENTION

In view of the above mentioned technical problems and technical requirements, a new type of lifting device needs to be designed. One aspect of the present invention is aimed at providing a lifting device, which is configured to lift or drop at least one load bearing mechanism. The lifting device includes a power driving mechanism and multiple lifting mechanisms connecting to the power driving mechanism. The power driving mechanism is configured to provide a driving force to the multiple lifting mechanisms. The multiple lifting mechanisms march the load bearing mechanism at least from a first height location to a second height location in a rolling manner under a function of the driving force provided by the power driving mechanism.

In the provided lifting device, at least one of the multiple lifting mechanisms includes a guide pillar and a loading carriage vehicle rolling up and down along the guide pillar. The loading carriage vehicle includes at least a first roller and a second roller. The guide pillar includes a first plane and a second plane that are disposed relatively, the first roller makes contact with the first plane in a rolling manner, and the second roller makes contact with the second plane in a rolling manner.

In the provided lifting device, a first gap is arranged between the first roller and the second plane, and a second gap is arranged between the second roller and the first plane.

In the provided lifting device, the first roller and the second roller are fixedly disposed between a first side wall of the loading carriage vehicle and a first side wall of the guide pillar.

In the provided lifting device, the loading carriage vehicle includes a first pair of rollers and a second pair of rollers, where the first pair of rollers and the second pair of rollers are separately disposed on two sides of the guide pillar. The first pair of rollers are fixedly disposed between the first side wall of the loading carriage vehicle and the first side wall of the guide pillar. The second pair of rollers are fixedly disposed between a second side wall of the loading carriage vehicle and a second side wall of the guide pillar.

In the provided lifting device, the at least one of the multiple lifting mechanisms includes an adjustable load bearing mechanism. The adjustable load bearing mechanism connects to and supports the load bearing mechanism, the adjustable load bearing mechanism includes a spindle connecting to the load bearing mechanism in a rotating manner and a spherical joint connecting to the spindle, and the spherical joint may rotate by a certain degree so as to allow the adjustable load bearing mechanism to adjust a height of the load bearing mechanism.

In the provided lifting device, the lifting device further includes a weight balance mechanism. The weight balance mechanism includes at least one weight balance piece, the at least one weight balance piece fixedly connects to the loading carriage vehicle, and the at least one weight balance piece exerts a fixed lifting force to partially withstand a weight force of the load bearing mechanism.

In the provided lifting device, the weight balance mechanism includes at least a first weight balance piece and a weight balance piece. The first weight balance piece and the second weight balance piece are symmetrically hung on two sides of the guide pillar of the lifting mechanism. The first weight balance piece fixedly connects to the loading carriage vehicle through a first connection link. The second weight balance piece fixedly connects to the loading carriage vehicle through a second connection link.

In the provided lifting device, the first connection link includes one pair of chains disposed in a parallel manner, the pair of chains mesh with one pair of gears, so as to drive the weight balance pieces to perform linear motion in a direction opposite to a motion direction of the loading carriage vehicle in a process that the loading carriage vehicle moves up and down.

In the provided lifting device, the at least one of the multiple lifting mechanisms includes a screw rod and a nut connecting to the load bearing mechanism. The screw rod drives, under a function of the driving force provided by the power driving mechanism, the nut to move, so as to march the load bearing mechanism at least from the first height location to the second height location.

In the provided lifting device, the screw rod is a trapezoidal screw rod. Another aspect of the present invention is aimed at providing an ultrasonic inspection system. The ultrasonic inspection system includes at least one ultrasonic probe and a lifting device, and the lifting device is configured to lift or drop at least a part of to-be-detected workpieces that are immersed in a liquid medium to a proper location, so that the ultrasonic probe can be conveniently used to perform ultrasonic inspection on the to-be-detected workpieces. The lifting device includes a power driving mechanism and a first lifting mechanism, a second lifting mechanism, and a third lifting mechanism that are connected to the power driving mechanism. The power driving mechanism provides a driving force to the first, second, and third lifting mechanisms. The first lifting mechanism defines a first vertical motion axis, the second lifting mechanism defines a second vertical motion axis, and the third lifting mechanism defines a third vertical motion axis. The first, second, and third lifting mechanisms drive, under a function of a driving force provided by the power driving system and in a basically synchronized manner, the to-be-detected workpieces to move up and down along the first, second, and third vertical motion axes. The first lifting mechanism includes a guide pillar and at least one pair of rollers, the at least one pair of rollers roll on a plane that is disposed relatively to the guide pillar, and an angle between an axis center connection line of the at least one pair of rollers and the first vertical motion axis may change.

In the provided ultrasonic inspection system, the power driving mechanism includes a general force source, a general coupling mechanism, a first branch coupling mechanism, a second branch coupling mechanism, a third branch coupling mechanism, a first gearbox, a second gearbox, a third gearbox, a fourth gearbox, and a fifth gearbox. The general coupling mechanism is connected between the general force source and the first gearbox, the first gearbox receives a general driving force provided by the general coupling mechanism and converts the general driving force into a first branch driving force, a second branch driving force, and a third branch driving force. The second gearbox is connected between the first gearbox and the fourth gearbox, and the third gearbox is connected between the first gearbox and the fifth gearbox. The first gearbox connects to a screw rod of a first lift mechanism by using the first branch coupling mechanism. The fourth gearbox connects to a screw rod of a second lift mechanism by using the second branch coupling mechanism. The fifth gearbox connects to a screw rod of a third lift mechanism by using the third branch coupling mechanism.

In the provided ultrasonic inspection system, the force source includes a motor and a decelerator.

Still another aspect of the present invention is aimed at providing an ultrasonic inspection system, where the ultrasonic inspection system includes at least one ultrasonic probe and a lifting device, the lifting device is configured to lift or drop at least a part of to-be-detected workpieces that are immersed in a liquid medium to a proper location, so that the ultrasonic probe can be conveniently used to perform ultrasonic inspection on the to-be-detected workpieces, the lifting device includes a power driving mechanism and a first lifting mechanism, a second lifting mechanism, and a third lifting mechanism that are connected to the power driving mechanism, the power driving mechanism provides a driving force to the first, second, and third lifting mechanisms, the first lifting mechanism defines a first vertical motion axis, the second lifting mechanism defines a second vertical motion axis, the third lifting mechanism defines a third vertical motion axis, the first, second, and third lifting mechanisms drives, under a function of a driving force provided by the power driving system and in a basically synchronized manner, the to-be-detected workpieces to move up and down along the first, second, and third vertical motion axes, the first lifting mechanism includes a first adjustable foot, the second lifting mechanism includes a second adjustable foot, the third lifting mechanism includes a third adjustable foot, the first, second, third adjustable feet separately connect to and support a workpiece bearing desk, and the first, second, third adjustable foot automatically adjust the workpiece bearing desk, so that the workpiece bearing desk is basically kept in a horizontal manner.

According to the lifting mechanisms provided in the present invention, multiple lifting mechanisms are disposed to move up and down in a rolling manner, which solves an interference problem that exists in an existing lifting mechanism. In addition, a weight balance mechanism is disposed to provide a lift force to withstand weight force of a support desk, which in one aspect helps use a drive motor of low power to provide a driving force, and further helps reduce an acting force undergone by a screw thread support plane of a screw rod nut precession mechanism to extend a service life of the screw rod nut precession mechanism. In addition, a foot support mechanism whose height can be adjusted is disposed to automatically adjust a height of a foot, so that the support desk basically keeps a support plane horizontal.

BRIEF DESCRIPTION OF DRAWINGS

The present invention may be understood in a better way by describing the implementation manners of the present invention with reference to the accompanying drawings, where in the accompanying drawings.

DETAILED DESCRIPTION

The following describes one or multiple specific implementation manners of the present invention. It should be noted first that in a specific description process of these implementation manners, for simplicity of description, the present specification may not describe in detail all features of practical implementation manners. It should be understood that, in an actual implementation process of any one implementation manner, as in a process of any one project or design project, in order to achieve the developers' specific goals, or in order to meet system-related or business-related limitations, various specific decisions may usually be made, and the decisions may change from one embodiment to another embodiment. In addition, it can also be understood that, although efforts made in the development process may be complicated and lengthy, for a person of ordinary skill in the art related to the content disclosed in the present invention, some changes, such as in design, manufacturing, or production, made based on the technical content disclosed in the disclosure are common technical means, and should be construed that the content of the disclosure is not sufficient.

Unless otherwise defined, the technical terms or scientific terms used in the specification and the claims should be the ordinary meaning understood by a person of ordinary skill in the technical field of the present invention. "First", "second" and similar words used in the present specification and the claims do not denote any order, quantity, or importance, but are just used to distinguish different components. "A" or "an" and other similar words do not denote quantity limitations, but denote that at least one exists. "Or" includes any one or all of listed items. "Comprises" or "comprising" and other similar words imply that an element or object appearing before the "comprises" or "comprising" covers enumerated elements or objects and equivalents elements thereof appearing after the "comprises" or "comprising", without excluding other elements or objects. In addition, terms indicating specific locations, such as "up", "down", "left", "right", "front", and "back", are descriptions with reference to specific accompanying drawings. Implementation manners disclose in the present invention may be placed in a manner different from that shown in the figures. Therefore, the location terms used herein should not be limited to locations described in specific embodiments.

Figure 1:
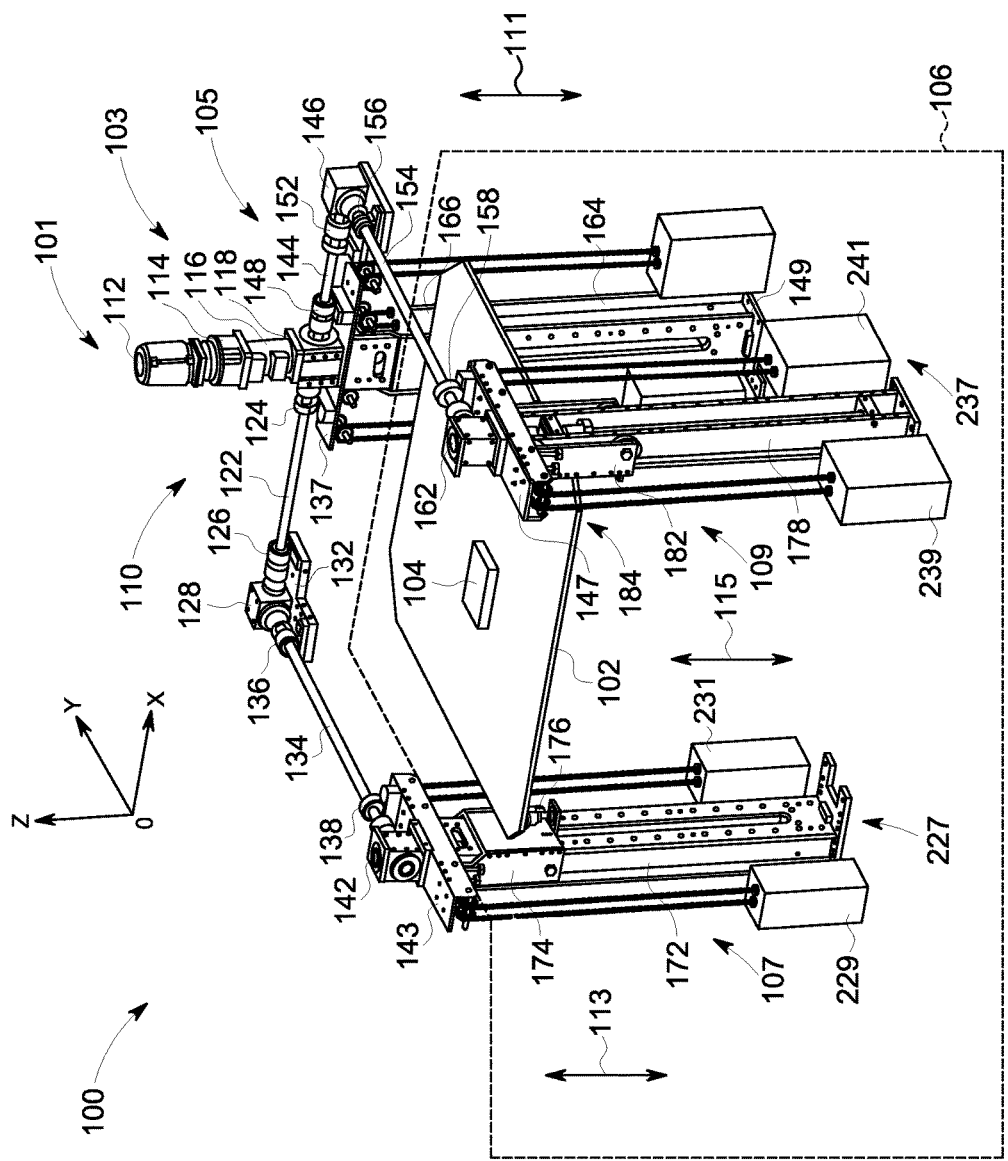
FIG. 1 shows a schematic stereogram of composition of at least one part of an implementation manner of a lifting device that is applied to an ultrasonic inspection system according to embodiments of the present invention.

First, referring to FIG. 1, which is a composition schematic of an implementation manner of a lifting device 110. In an implementation manner, the lifting device 110 is applied to an ultrasonic inspection system 100. The lifting device 110 supports a to-be-detected workpiece 104 by using a support mechanism 102 (such as a support desk), and may drive the support mechanism 102 to move up and down so as to drive the to-be-detected workpiece 102 to move correspondingly, so that an ultrasonic probe (not shown in the figure) can be conveniently used to perform ultrasonic imaging, and therefore a health condition of the to-be-detected workpiece 104 can be inspected, that is, whether a defect (such as a break, a crack, and a bubble) exists. The to-be-detected workpiece 104 shown in FIG. 1 is only used as an example and includes but is not limited to a vehicle wheel, turbine motor blade, a steel plate, an aluminum plate, a steel pipe, and the like. Generally, in some implementation manners, the to-be-detected workpiece 102 is partially or completely immersed in a liquid medium (such as water, which is indicated by a dashed line 106 in the figure), so that an ultrasonic wave transmitted by the ultrasonic probe and/or a return ultrasonic wave reflected by the to-be-detected workpiece 104 may be transmitted along the liquid medium.

As shown in FIG. 1, the lifting device 110 includes a power driving mechanism 101 and multiple lifting mechanisms 103. The power driving mechanism 101 is configured to provide a driving force to the multiple lifting mechanisms 103, so that the multiple lifting mechanisms 103 performs a lift or drop motion, the load bearing mechanism 102 connecting to the multiple lift-drop mechanisms 103 can be correspondingly lifted or dropped to different height locations, and therefore the ultrasonic probe can be conveniently used to perform ultrasonic inspection on the to-be-detected workpiece 104 placed on the load bearing mechanism 102.

In some specific implementation manners, the multiple lifting mechanisms 103 include three groups of lifting mechanisms, that is, a first lifting mechanism 105, a second lifting mechanism 107, and a third lifting mechanism 109. The three groups of the lifting mechanisms 105, 107, and 109 are separately disposed in a triangular shape, so as to support more steady support for the load bearing mechanism 102. Certainly, in another implementation manner, a person of ordinary skill in the art should understand that it may also be that a group of lifting mechanisms is used, or two groups of lifting mechanisms are used, or more than three groups lifting mechanisms are used to lift or drop the load bearing mechanism 102.

In some specific implementation manners, the power driving mechanism 101 and the three groups of the lifting mechanisms 105, 107, and 109 are specially disposed, so that the three groups of the lifting mechanisms 105, 107, and 109 drive, in a basically synchronized manner, the load bearing mechanism 102 to move up and down. The first lifting mechanism 105 defines a first vertical motion axis (shown by an arrow 111 in the figure), the second lifting mechanism 107 defines a second vertical motion axis (shown by an arrow 113 in the figure), and the third lifting mechanism 109 defines a third vertical motion axis (shown by an arrow 115 in the figure). In an implementation manner, the first, second, and third vertical motion axes 111, 113, and 115 are disposed in a mutually parallel manner. The three groups of the lifting mechanisms 105, 107, and 109 may be driven to move in a same speed along the three vertical motion axes 111, 113, and 115, that is, move up and down. In some implementation manners, the load bearing mechanism 102 may connect to the three groups of the lifting mechanisms 105, 107, and 109 in any proper mechanism connection manner.

Further referring to FIG. 1, in an implementation manner, the power driving mechanism 101 includes a general force source 112, where the general force source 112 is configured to provide a general driving force so as to drive the above mentioned three groups of the lifting mechanisms 105, 107, and 109. The power driving mechanism 101 further includes multiple force transmission components connecting to the general force source 112. The general force source 112 may be separately converted, by using the multiple force transmission components, into driving forces that are suitable for the lifting mechanisms 105, 107, and 109. In an implementation manner shown in FIG. 1, the general force source 112 includes a single drive motor, which may convert electric energy into mechanical energy to provide a mechanical driving force. In another implementation manner, the general force source 112 may also include multiple independent drive motors. For example, in some implementation manners, the general force source 112 may include a first motor which is configured to provide a first driving force to the first lifting mechanism 105, a second motor which is configured to provide a second driving force to the second lifting mechanism 107, and a third motor which is configured to provide a third driving force to the third lifting mechanism 109. In this case, the three motors may be controlled to work in a synchronized manner, so as to drive the lifting mechanisms that are separately connecting to the three motors to perform a lift or drop motion, and drive the corresponding load bearing mechanism 102 to move.

Figure 2:
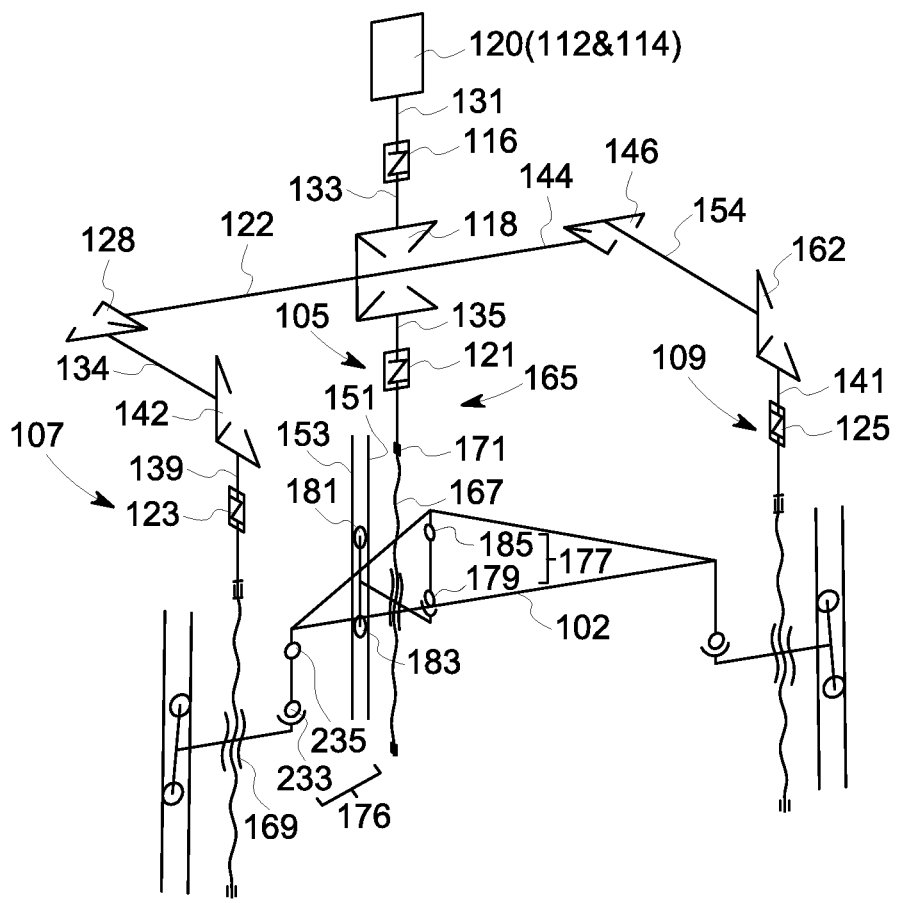
FIG. 2 shows a simplified diagram of a mechanism of an implementation manner of a lifting device shown in FIG. 1.

Referring to both FIG. 1 and FIG. 2, in an implementation manner, the power driving mechanism 101 includes a general gearbox (or also called a decelerator) 114, a general coupling mechanism 116, a first gearbox 118, a second gearbox 128, a third gearbox 146, a fourth gearbox 142, a fifth gearbox 162, a first branch coupling mechanism 121, a second branch coupling mechanism 123, and a third branch coupling mechanism 125. For ease of description, in an implementation manner, for example, the first branch coupling mechanism 121, the second branch coupling mechanism 123, and the third branch coupling mechanism 125 are used as a part of the power driving mechanism 101. Certainly, it may be understood that in another implementation manner, the first branch coupling mechanism 121, the second branch coupling mechanism 123, and the third branch coupling mechanism 125 may also be grouped as a part of the first lifting mechanism 105, the second lifting mechanism 107, and the third lifting mechanism 109. In FIG. 2, the general gearbox 114 and the general force source 112 are equivalent to a force module 120. The force module 120 connects to the first gearbox 118 by using the general coupling mechanism 116. In an implementation manner, the general coupling mechanism 116 may be a specific elastic mechanism, and it can be ensured that even when axial direction deviation occurs in an output axis 131 of the force module 120 and an input axis 131 of the first gearbox 118, the general coupling mechanism 116 may also keep rotation stable. In an implementation manner, the force module 120, the general coupling mechanism 116, and the first gearbox 118 are disposed on a first support plate 137.

Further referring to FIG. 1 and FIG. 2, the first gearbox 118 receives, through an input axis 133, a general force provided by the force module 120 that includes 112 the general force source 112 and the decelerator 114, and resolves the general force into the first driving force, the second driving force, and the third driving force. The first driving force is transmitted along a negative direction of an OZ axis shown in FIG. 1 and is exerted on the first branch coupling mechanism 121 through a first drive output axis 135; the second driving force is transmitted along a negative direction of an OX axis shown in FIG. 1 and is exerted on the second gearbox 128 through a second force output axis 122; and the third driving force is transmitted along a positive direction of the OX axis shown in FIG. 1 and is exerted to the third gearbox 146 through a third force output axis 144. In an implementation manner shown in FIG. 1, two ends of the second power driving axis 122 separately pass through through-holes (not shown in the figure) disposed on a first bearing part 124 and a second bearing part 126 and are supported by the two bearing parts 156 and 158. The first bearing part 124 is installed on the above mentioned first support plate 137, and the second bearing part 126 is installed on a first fixing block 132. The first fixing block 132 may further be installed on the lifting mechanism 100 or another object of the ultrasonic inspection system 100, such as a container containing a liquid medium (not shown in the figure).

Further referring to FIG. 1 and FIG. 2, the second gearbox 128 is disposed to convert the driving force that is exerted by the second force output axis 122 and is transmitted along the negative direction of the OX axis to a driving force that is transmitted along a negative direction of an OY axis, that is, the driving force is turned left 90 degrees, and exerts the driving force on the fourth gearbox 142 through a fourth force output 134. The fourth gearbox 142 is disposed to convert the driving force that is exerted by the fourth force output 134 into a driving force that is transmitted along the negative direction of the OZ axis and exerts the driving force to the second branch coupling mechanism 123 through a fifth force output axis 139 (shown in FIG. 2). In an implementation manner, two ends of the fourth force output axis 134 separately pass through through-holes (not shown in the figure) disposed on a third bearing part 136 and a fourth bearing part 138 and are supported by the two bearing parts 136 and 138. The third bearing part 136 is installed on the first fixing block 132, and the fourth bearing part 138 is installed on a second support plate 143. In addition, the fourth gearbox 142 is also installed on the second support plate 143.

Further referring to FIG. 1 and FIG. 2, the third gearbox 146 is disposed to convert the driving force that is exerted by the third force output axis 144 and is transmitted along the positive direction of the OX axis to a driving force that is transmitted along the negative direction of the OY axis, that is, the driving force is turned right 90 degrees, and exerts the driving force on the fifth gearbox 162 through a sixth force output axis 154. In an implementation manner shown in FIG. 1, two ends of the third power driving axis 144 separately pass through through-holes (not shown in the figure) disposed on a fifth bearing part 148 and a sixth bearing part 152 and are supported by the two bearing parts 148 and 152. The fifth bearing part 148 is installed on the above mentioned first support plate 137, and the sixth bearing part 152 is installed on a second fixing block 145. The third gearbox 146 may also be installed on the second fixing block 145, and the second fixing block 145 may further be installed on the lifting mechanism 100 or another object of the ultrasonic inspection system 100, such as a container containing a liquid medium (not shown in the figure). The fifth gearbox 162 is disposed to convert the driving force that is exerted by the sixth force output axis 154 into a driving force that is transmitted along the negative direction of the OZ axis and exerts the driving force to the third branch coupling mechanism 125 through a seventh force output 141 (shown in FIG. 2). In an implementation manner, two ends of the sixth force output axis 154 separately pass through through-holes (not shown in the figure) disposed on a seventh bearing part 156 and an eighth bearing part 158 and are supported by the two bearing parts 156 and 158. The seventh bearing part 156 is installed on the second fixing block 145, and the eighth bearing part 158 is installed on a third support plate 147. In addition, the fifth gearbox 162 is also installed on the third support plate 147.

Further referring to FIG. 1 and FIG. 2, the first lifting mechanism 105 includes a first guide pillar 164 and a first loading carriage vehicle 166. As shown in FIG. 1, one end or an upper end of the first guide pillar 164 connects to the second support plate 143 and provides support for the second support plate 143 and various components (such as a bearing part and a gearbox) that are installed on the second support plate 143; and the other end or a lower end of the first guide pillar 164 connects to a support base 149 and is placed, by using the support base 149, on a proper support plane (such as a bottom plane of a container containing a liquid medium). In an implementation manner, the first guide pillar 164 is disposed in a vertical manner and defines the first vertical motion axis 111, so that the first loading carriage vehicle 166 moves up and down along the first vertical motion axis 111 under a function of a driving force.

Figure 3:
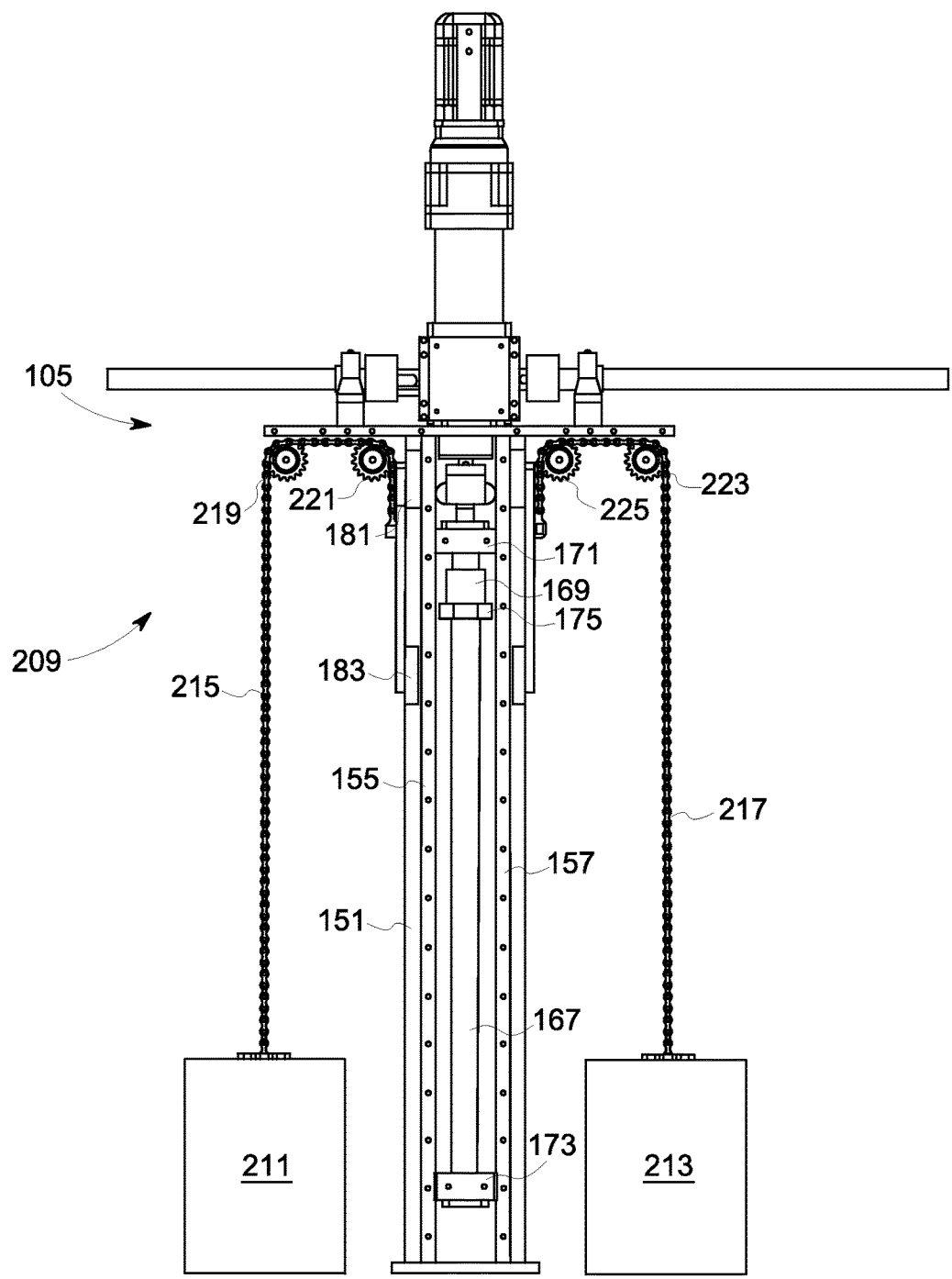
FIG. 3 shows a partial schematic diagram of a lifting mechanism in a lifting device shown in FIG. 1.
Figure 4:
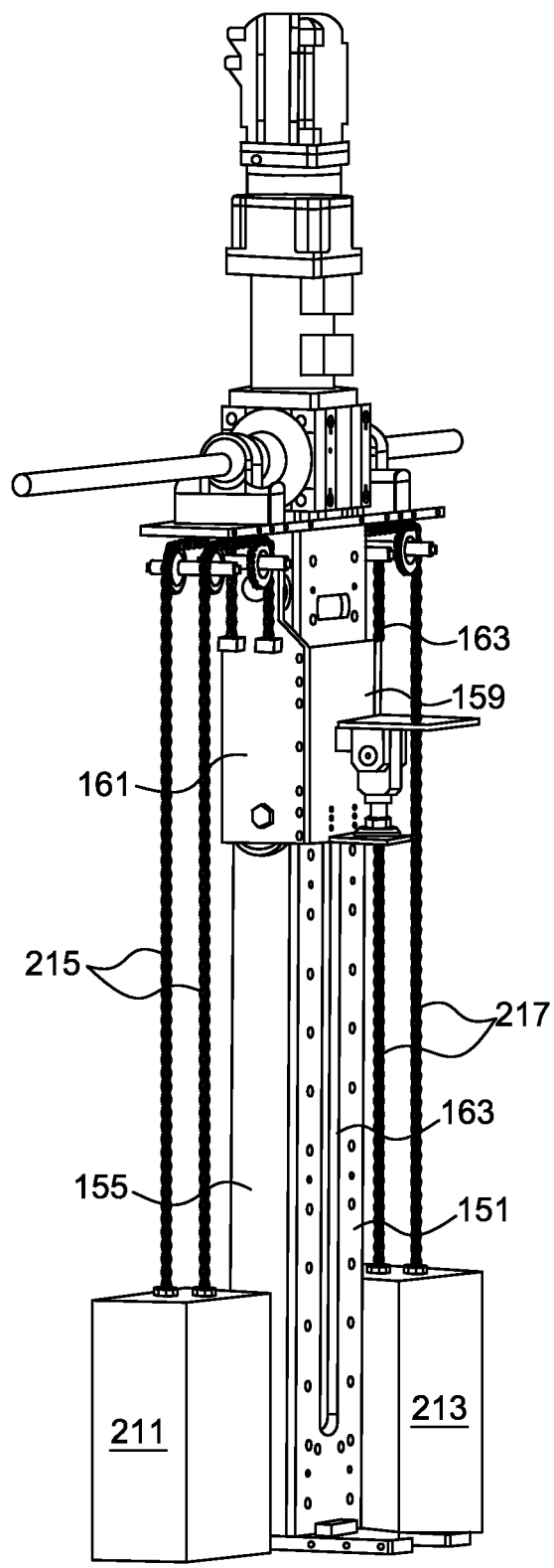
FIG. 4 shows a schematic stereogram of a lifting mechanism in a lifting device shown in FIG. 1 from another perspective.

Further referring to FIG. 3 and FIG. 4, the first guide pillar 164 includes a first panel 151, a second panel 153, a first side panel 155, and a second side panel 157. The first panel 151 and the second panel 153 are disposed in a mutually parallel manner, and the first side panel 155 and the second side panel 157 are disposed in a mutually parallel manner. In addition, the first side panel 155 and the second side panel 157 are vertically connected between the first panel 151 and the second panel 153 to form a vertical containing space, so as to contain all force transmission mechanism components inside the containing cavity. In an implementation manner, a part of the middle of the first panel 151 is hollowed out to form a long and narrow groove 163. The groove 163 is configured for a connection component to pass through, so as to fixedly connect the force transmission mechanism and the first loading carriage vehicle 166, and the connection component may freely move up and down inside the groove 163. In an implementation manner, a certain gap is arranged between locations in which the first side panel 155 and the second side panel 157 respectively connect to the first panel 151 and the second panel 153 and edge locations of the first panel 151 and the second panel 153, so that spindly planes are defined and the first loading carriage vehicle 166 moves along these spindly planes.

Referring to both FIG. 1 and FIG. 4, in an implementation manner, the first loading carriage vehicle 166 includes a first side wall 159, a second side wall 161, and a third side wall 163. The second side wall 161 and the third side wall 163 vertically connect to two sides of the first side wall 159, so as to form a U-shape structure with one open end. The U-shape structure is disposed on the first guide pillar 164, so that the first side wall 159 is parallel to the first panel 151 of the first guide pillar, and a certain gap exists between the two. The second side wall 161 is parallel to the first side panel 155 of the first guide pillar 164, and a certain gap also exists between the two. The third side wall 163 is parallel to the second side panel 157 of the first guide pillar 164, and a certain gap exists between the two.

Figure 5:
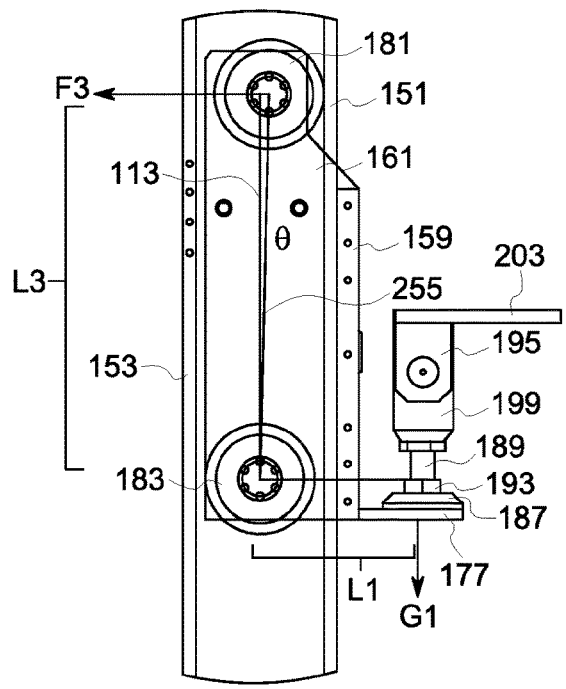
FIG. 5 shows another partial schematic diagram of a lifting mechanism in a lifting device shown in FIG. 1.

Further referring to FIG. 5, in an implementation manner, a first roller 181 and a second roller 183 are separately installed on two ends of the second side wall 153 of the first loading carriage vehicle 166. The first roller 181 is disposed between an inner side of the second side wall 153 and an external side wall of the first side panel 155 of the first guide pillar 164. In some implementation manners, a gasket, such as a brass article, may be installed between the first roller 181 and the inner side of the second side wall 153 and/or between the first roller 181 and the first side panel 155, so as to reduce abrasion and noises. In some implementation manners, an external roller plane of the first roller 181 makes contact with the first panel 151 and may roll relatively to the first panel 151. Similarly, an external roller plane of the second roller 183 makes contact with the first panel 151 and may roll relatively to the second panel 153. Specifically, a certain gap is arranged between the first roller 181 and an inner side wall of the second panel 153, and a certain gap is arranged between the second roller 183 and an inner side wall of the first panel 151. It may be understood that such gaps arranged between the first and second rollers 181 and 183 and the panels 153 and 151 that are relative to the first and second rollers 181 and 183 may allow the first loading carriage vehicle 166 to adapt to the first panel 151 and the second panel 153 that have irregular shapes.

Figure 6:
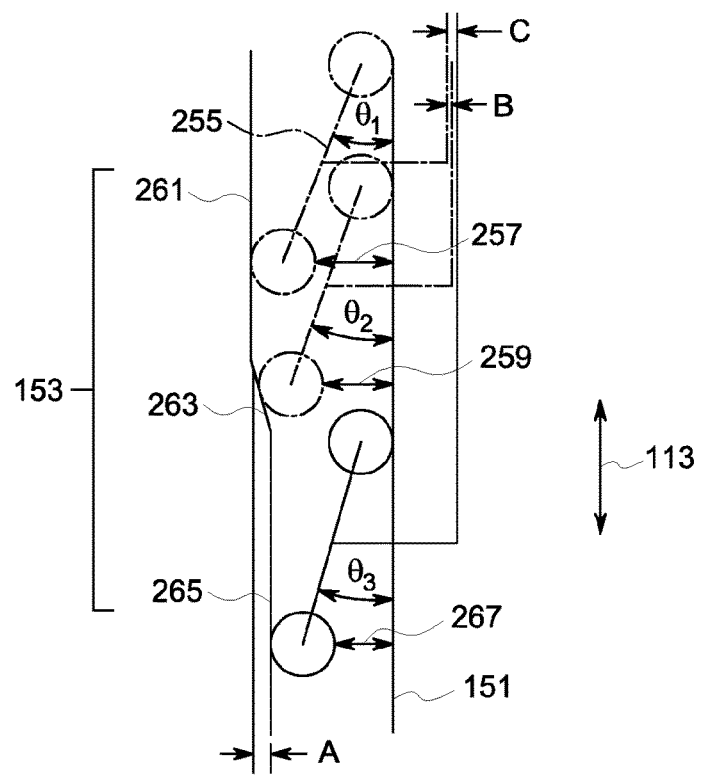
FIG. 6 shows a schematic diagram of an running state of a roller in a lifting mechanism shown in FIG. 5.

To be more specific, in some cases, because an error exists in a processing procedure, for example, as shown in FIG. 6, a plane of the second panel 153 that is contacted by the second roller 183 may not be a complete flat plane, for example, the second panel 153 includes a first segment 261, a second segment 263, and a third segment 265. The first segment 261 is parallel to the first panel 151. Therefore, when the second roller 183 rolls along the first segment 261, a first angle $\theta1$ exists between an axis center connection line 255 between the first and second rollers 181 and 183 and the first panel 151 or the first vertical motion axis 113, and a first gap 257 exists between the second roller 183 and the first plane 151. Because the first segment 261 is a plane that is parallel to the first plane 151, the first angle $\theta1$ remains unchanged and the first gap 257 also remains unchanged basically. The second roller 183 keeps rolling down and moves to the second segment 263. Because the second segment 263 is a tilt plane that is unparallel to the first segment 261, in a location on the second segment 263, a second angle $\theta1$ that is less than the first angle $\theta2$ exists between the axis center connection line 255 between the first and second rollers 181 and 183 and the first panel 151 or the first vertical motion axis 113, and a second gap 259 that is less than the first gap 257 between the second roller 183 and the first plane 151. When the second roller 183 keeps rolling along the second segment 263, the second angle $\theta2$ becomes smaller and the second gap 259 also becomes smaller. When the second roller 183 moves to the third segment 265, because the third segment 265 is a plane that is parallel to both the first segment 261 and the first panel 151, a third angle $\theta3$ exists between the axis center connection line 255 between the first and second rollers 181 and 183 and the first panel 151 or the first vertical motion axis 113, and a third distance 267 exists between the second roller 183 and the first plane 151. When the second roller 183 keeps rolling down, the third angle $\theta3$ keeps unchanged and the third distance 267 keeps unchanged. Therefore, by flexibly adjusting the angle between the axis center connection line 255 between the first and second rollers 181 and 183 and the first panel 151 or the first vertical motion axis 113, interference that is between the roller and the panel and causes deadlock of the first loading carriage vehicle 166 can be avoided.

In addition, in some implementation manners, the first and second rollers 181 and 183 may be disposed, so that a torque undergone by the first loading carriage vehicle 166 is balanced. As shown in FIG. 5, a force that is exerted by the load bearing mechanism or support desk 102 to the first loading carriage vehicle 166 is G1, and an arm of the force is L1; and a counter-acting force undergone when the first roller 181 makes contact with the first panel 151 of the guide pillar is F3, and an arm of the force is L3. Therefore, when the following formula (1) is met, it can be ensured that the torque is balanced:

$$G_1 {}^*L_1 = F_3 {}^*L_3, \qquad (1)$$

In an implementation manner shown in the figure, similarly, rollers (not numbered in the figure) are separately installed on two sides of the third side wall 155 of the first loading carriage vehicle 166. The pair of rollers are disposed between an inner side of the third side wall 155 and an external side wall of the second side panel 157 of the first guide pillar 164. In another implementation manner, the pair of rollers may also be omitted, or in another implementation manner, the first loading carriage vehicle 166 may further include multiple pairs of rollers.

Figure 7:
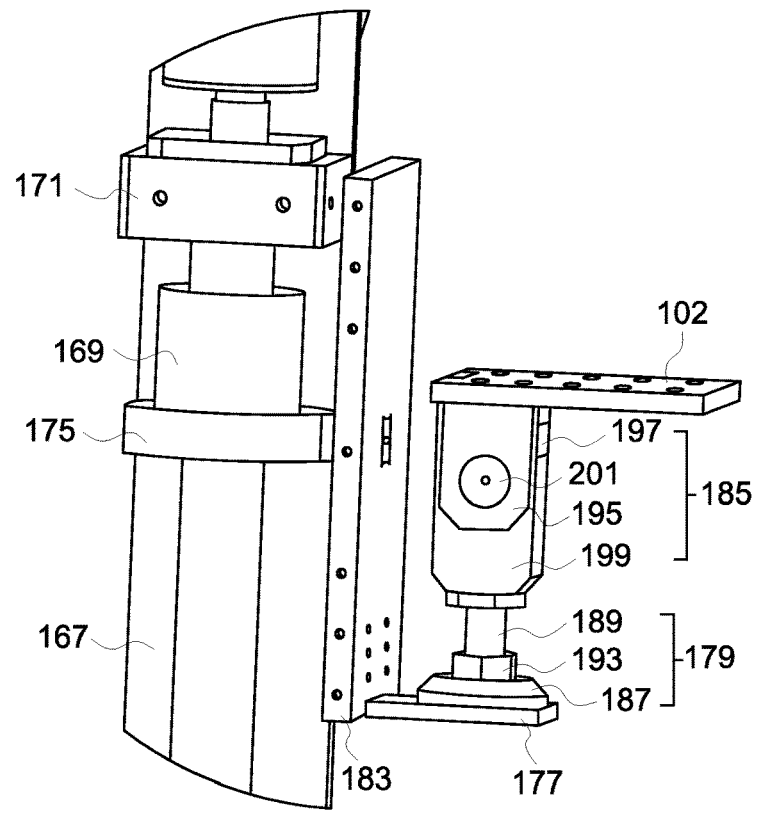
FIG. 7 shows a schematic stereogram of a force transmission mechanism of a lifting mechanism in a lifting device shown in FIG. 1.
Figure 8:
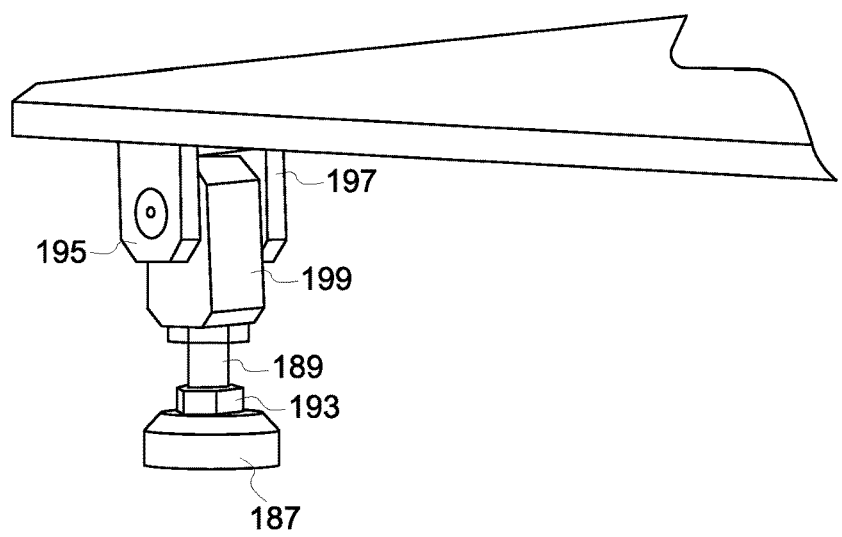
FIG. 8 shows a schematic stereogram of an adjustable support foot that is applied to a lifting device shown in FIG. 1.
Figure 9:
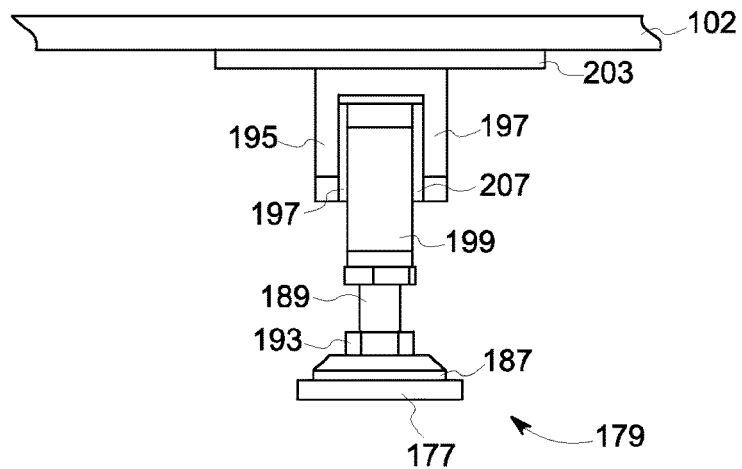
FIG. 9 shows a schematic diagram of a side surface of an adjustable support foot that is applied to a lifting device shown in FIG. 1.
Figure 10:
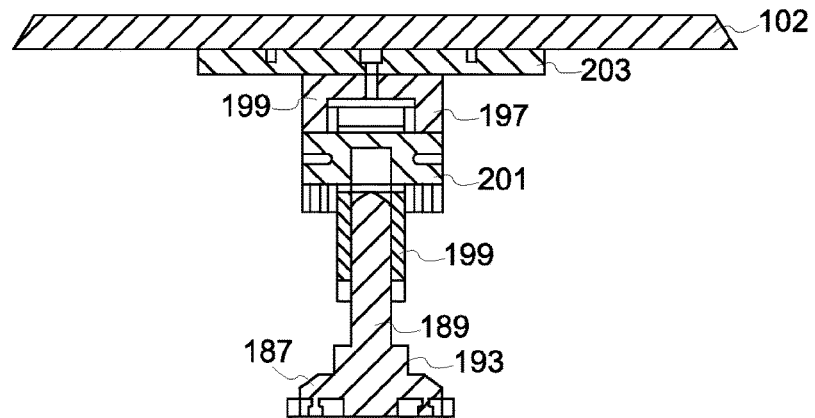
FIG. 10 shows a schematic diagram of a rotating state of an adjustable support foot that is applied to a lifting device shown in FIG. 1.

Further referring to FIG. 1, FIG. 2, and FIG. 7, the first lifting mechanism 105 includes a first force transmission mechanism 165. The first force transmission mechanism 165 connects to the first gearbox 118 by using the first force output axis 135, so as to receive a driving force transferred by the first force output axis and carry, under a function of the driving force, the first loading carriage vehicle 166 to perform a lift or drop motion. To be more specific, in a specific=implementation manner, the first force transmission mechanism 165 includes a first screw rod 167 and a first nut 169. The first screw rod 167 is basically a spindly cylinder which extends along the first vertical motion axis 111 and is disposed to be basically parallel to the first vertical motion axis 111. A first end or an upper end of the first screw rod 167 passes through the first fixing part 171 and connects to the first branch coupling mechanism 121, where the first fixing part 171 is fixedly connected between the first side panel 155 and the second side panel 157. A second end or a lower end of the first screw rod 167 passes through a second fixing part 173, where the second fixing part 173 is fixedly connected between the first side panel 155 and the second side panel 157. In addition, an external screw thread is arranged on an external surface of the first screw rod 167.

In a specific implementation manner, the external screw thread has a trapezoidal screw thread section. The first nut 169 is a hollow cylinder whose inner surface is arranged with an inner screw thread, and the inner screw thread may screw with the external screw thread of the first screw rod 167. It may be understood that the screw rod which is disposed with the trapezoidal section enables the force transmission mechanism to have a self-lock function. That is, even when no driving force is exerted on the first screw rod 167, a downward motion of the first nut 169 under a function of external weight can be avoided.

Further referring to FIG. 7, in an implementation manner, the first force transmission mechanism 165 further includes a first middleware 175. One end of the first middleware 175 is a hollow cylinder which is disposed on the first screw rod 167 and connects to the first nut 169; and the other end of the first middleware 175 is a tongue-shape part. The tongue-shape part extends externally from a side of the cylinder, and the bottom of the tongue-shape part is inserted into a first through-hole disposed on the first side wall 159 of the first loading carriage vehicle 166 and more particularly uses interference fit, so that the first nut 169, the first loading carriage vehicle 166, and the first middleware 175 are fixedly connected. Therefore, when the first screw rod 167 rotates under a function of a driving force provided by the first force output axis 135, the first screw rod 167 drives the first nut 169 to rotate. The first screw rod 167 cannot move up and down due to restriction of the first fixing part 171 and the second fixing part 173, and therefore the first nut 169 simultaneously performs a linear motion in upward and downward directions, that is, a direction of the first vertical motion axis 111. The first middleware 175 connects to the first nut 169, and therefore the first nut 169 drives the first middleware 175 to move up and down. Further, the first side wall 153 of the first loading carriage vehicle 166 fixedly connects to the first middleware 175, and therefore the first loading carriage vehicle 166 is also driven to move up and down. To be more specific, the first loading carriage vehicle 166 rolls on a surface of the guide pillar 164 by using the multiple disposed rollers, such as the first roller 181 and the second roller 183.

Returning to refer to FIG. 1 and further referring to FIG. 7 to FIG. 10, the first loading carriage vehicle 166 further fixedly connects to a first adjustable foot 168, where the first adjustable foot 168 further connects to the load bearing mechanism 102 and flexibly provides support for the load bearing mechanism 102. To be more specific, a gap or a through-hole is disposed on a lower edge of the first side wall 159 of the first loading carriage vehicle 166, so that one end of a first slab-shape connection part 177 is inserted into the gap or the through-hole. Specifically, in some implementation manners, the first slab-shape connection part 177 is inserted into the gap or the through-hole in an interference fit manner, so that the first adjustable foot 168 is fixedly connected. A rotation part 179 and a rotation axis part 185 connecting to the rotation part 179 are fixedly disposed on the slab-shape connection part 177. In an implementation manner, the rotation part 179 is a spherical joint which includes a base 187 and a rotation rod 189. The base 187 is fixedly installed on the slab-shape first connection part 177, and a dent 191 is disposed in the middle part of the base 187. The dent has a spherical surface, so that an end part of the rotation rod 189 is contained in the dent, makes contact with the spherical surface, and performs a relative motion of a direction of 360 degrees. In an implementation manner, a limiting nut 193 is disposed near a lower end part of the rotation rod 189, where the limiting nut 193 may be adjusted to different heights so as to limit a rotation angle for the rotation rod 189 relative to the base 187. In an implementation manner, the limiting nut 193 is arranged so that a maximum rotation angle for the rotation rod 189 relative to the base 187 is around 30 degrees. In another implementation manner, the rotation angle for the rotation rod 289 relative to the base 187 may also be greater than 30 degrees or less than 30 degrees.

Further referring to FIG. 7 to FIG. 10, the rotation axis part 185 includes a first bearing part 195, a second bearing part 197, a third bearing part 199, and a rotation axis 201. Both the first bearing part 195 and the second bearing part 197 are fixedly installed on a second slab-shape connection part 203, where the second slab-shape connection part 203 is further fixedly installed on a corner of the support desk 102. The first bearing part 195 and the second bearing part 197 are disposed in a mutually parallel manner and through-holes or blind holes for the rotation axis 201 to pass through are disposed on the two, so that two end parts of the rotation axis 201 can pass through the through-holes or are contained in the blind holes. A through-hole is disposed on one end of the third bearing part 199, so that the rotation axis 201 passes through the through-hole, and the second bearing part 199 is disposed between the first bearing part 195 and the second bearing part 197. In some implementation manners, the rotation axis part 185 may further include a first gasket 205 and a second gasket 207, where the first gasket 205 is disposed between the first bearing part 195 and the third bearing part 199, and the second gasket 207 is disposed between the second bearing part 197 and the third bearing part 199. In a specific implementation manner, the first gasket 205 and the second gasket 207 may be brass articles which can reduce abrasion and noises. The other end or a lower end of the third bearing part 199 fixedly connects to one end or an upper end of the rotation rod 189 of the rotation part 179. Specifically, in an implementation manner, the rotation axis part 185 of the first adjustable foot 168 is disposed to drive the support desk 102 to perform a rotation motion on a first coordinate plane, that is, an O-YZ plane.

Returning to refer to FIG. 1 and further referring to FIG. 3, the first lifting mechanism 105 further includes a first weight balance mechanism 209, where the first weight balance mechanism 209 connects to the first loading carriage vehicle 166. The first loading carriage vehicle 166 is configured to exert a constant lift force on the first loading carriage vehicle 166, so as to partially offset weight that is exerted by the load bearing mechanism 102 and undergone by the first loading carriage vehicle 166. It is beneficial to dispose such a weight balance mechanism 209, so that only a motor with relatively lower power or driving force can be used to drive the load bearing mechanism 102 to perform a lift or drop motion. In addition, the lift force exerted by the first weight balance mechanism 209 may reduce stress that is exerted by the load bearing mechanism 102 and undergone by the external screw thread surface of the screw rod in the first force transmission mechanism 165, so as to avoid excessive wear on the external screw thread surface of the screw rod, that is, a service life of the first force transmission mechanism 165 can be extended.

Figure 12:
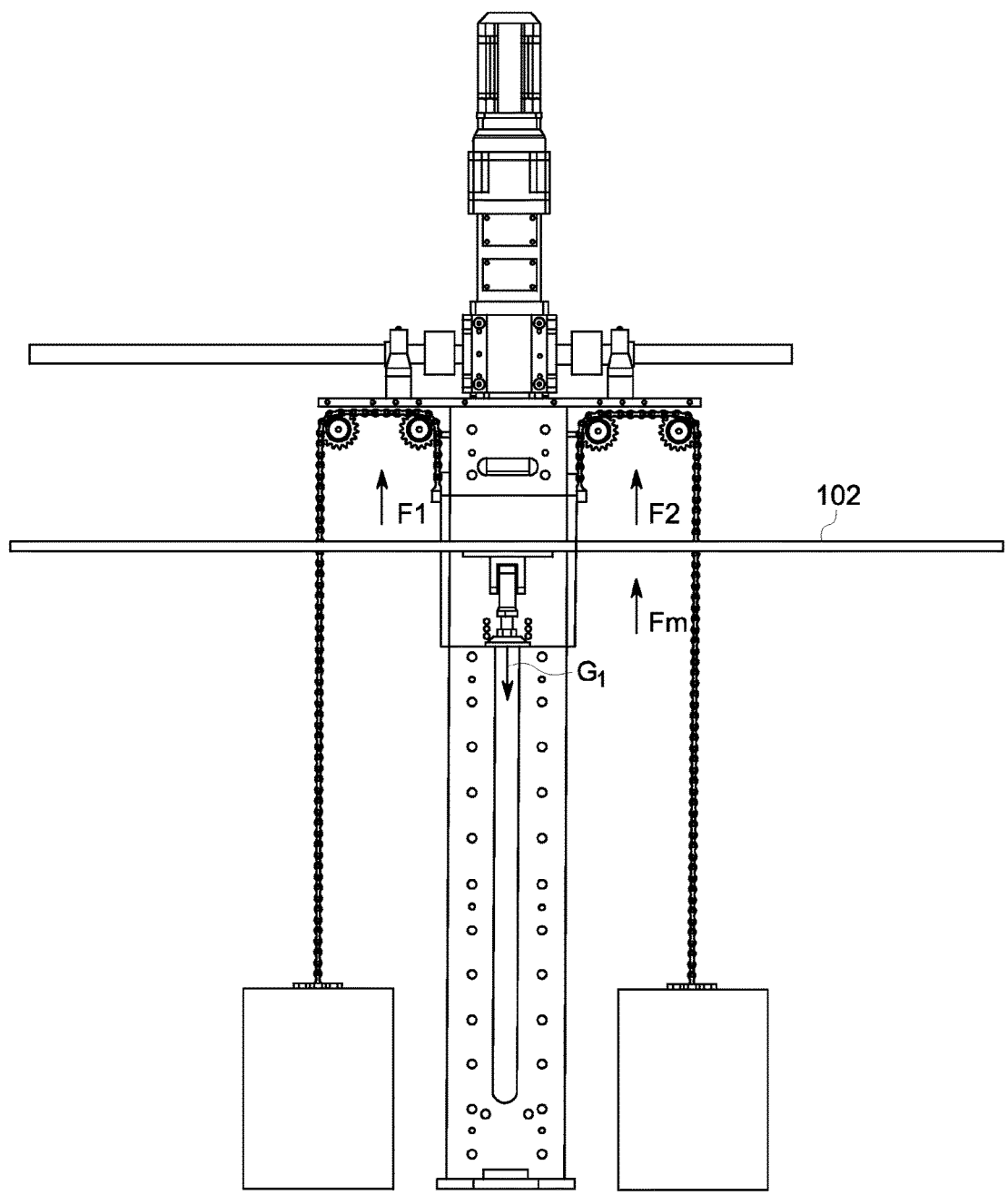
FIG. 12 shows a schematic diagram of a stress of a lifting mechanism shown in FIG. 1.

In a specific implementation manner, the first weight balance mechanism 209 includes a first weight balance piece 211 and a second weight balance piece 213. The first weight balance piece 211 and the second weight balance piece 213 are hung on two sides of the first guide pillar 164 in a symmetrical manner. As shown in FIG. 12, it is assumed that a force exerted by the first weight balance piece 211 on the first loading carriage vehicle 166 is F1, a force exerted by the second weight balance piece 213 on the first loading carriage vehicle 166 is F2, and weight of load bearing mechanism or the support desk undergone by the first loading carriage vehicle is G1. When the following formula (2) is met, the first loading carriage vehicle 166 can be lifted to perform an upward motion:

$$F_1+F_2+F_m\ge G_1, \quad (2);$$

and when the following formula (3) is met, the first loading carriage vehicle 166 can be dropped to perform a downward motion:

$$F_1+F_2, F_m+G_1, \quad (3),$$

where $F_m$ is a driving force exerted by the first force transmission mechanism on the first loading carriage vehicle 166. In an implementation manner, the first weight balance piece 211 connects to an external side of the second side wall 153 of the first loading carriage vehicle 166 by using a first connection link 215. The first connection link 215 includes a pair of chains that are disposed in a parallel manner, and in another implementation manner, the first connection link 215 may also include one chain or more than two chains. The pair of chains 215 are disposed on a pair of gears 219 and 221 that are disposed separately along a direction of the OX axis. Similarly, the second connection link 217 also includes a pair of chains that are disposed in a parallel manner, where the pair of chains 217 are disposed on a pair of gears 223 and 225 that are separately disposed along the direction of the OX axis. It may be understood that it is beneficial for the first lifting mechanism 105 that two chains are set to connect the first weight balance piece 211 or the second weight balance piece 213 and the first loading carriage vehicle 166, so that the weight balance piece can be prevented from hitting the ground or the container bottom when a chain is parted.

Returning to refer to FIG. 1, a structure of the second lifting mechanism 107 is similar to that of the first lifting mechanism 105. For example, the second lifting mechanism 107 includes a second guide pillar 172, a second loading carriage vehicle 174, and a second adjustable foot 176. The second loading carriage vehicle 174 drives, under a function of a second power driving mechanism (whose specific structure is the same as the first power driving mechanism 165 shown in FIG. 2) that is placed inside the second guide pillar 172, the second loading carriage vehicle 174 to move up and down or roll along the second vertical motion axis 113. The second loading carriage vehicle 174 further drives the second adjustable foot 176 and the load bearing mechanism or support desk 102 to move up and down, so as to move the to-be-detected workpieces 104 to different height locations. Similarly, the second lifting mechanism 107 further includes a second weight balance mechanism 227, where the second weight balance mechanism 227 includes a pair of weight balance pieces 229 and 231 that are symmetrically disposed on two sides of the second guide pillar 172.

A structure of the second adjustable foot 176 of the second lifting mechanism 107 is the same as that of the first adjustable foot 168 of the first lifting mechanism 105. For example, as shown in FIG. 2, the second adjustable foot 176 includes a rotation part 233 and a rotation axis part 235. A difference lies in that the rotation axis part 233 of the second adjustable foot 176 is disposed to run in a second coordinate plane, that is, performs a rotation motion on an O-XZ plane, where the O-XZ plane is perpendicular to the O-YZ plane.

Returning to refer to FIG. 1, a structure of the third lifting mechanism 109 is also similar to that of the first lifting mechanism 105. For example, the third lifting mechanism 109 includes a third guide pillar 178, a third loading carriage vehicle 182, and a third adjustable foot 184. The third loading carriage vehicle 182 drives, under a function of a third power driving mechanism (whose specific structure is the same as the first power driving mechanism 165 shown in FIG. 7) that is placed inside the third guide pillar 178, the third loading carriage vehicle 182 to move up and down or roll along the third vertical motion axis 115. The third loading carriage vehicle 182 further drives the third adjustable foot 184 and the load bearing mechanism or support desk 102 to move up and down, so as to move the to-be-detected workpieces 104 to different height locations. Similarly, the third lifting mechanism 109 further includes a third weight balance mechanism 237, where the third weight balance mechanism 237 includes a pair of weight balance pieces 239 and 241 that are symmetrically disposed on two sides of the third guide pillar 178.

Figure 11:
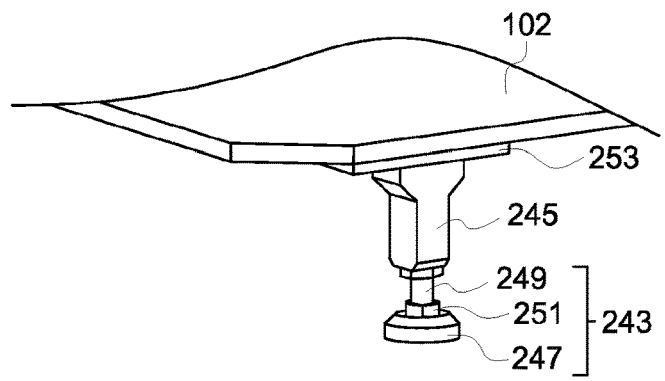
FIG. 11 shows a schematic stereogram of another adjustable support foot that is applied to a lifting device shown in FIG. 1.

A structure of the third adjustable foot 184 of the third lifting mechanism 109 is different from those of the first adjustable foot 168 of the first lifting mechanism 105 and the second adjustable foot 168 of the second lifting mechanism 107. As shown in FIG. 11, the third adjustable foot 184 includes a rotation part 243 and a fixing part 245. The rotation part 243 is the same as that of the first and second adjustable feet 168 and 176 and includes a base 247 and a rotation rod 249. In an implementation manner, a limiting nut 251 is disposed near a lower end part of the rotation rod 249, where the limiting nut 251 may be adjusted to different heights so as to limit a rotation angle for the rotation rod 249 relative to the base 247. In an implementation manner, an upper end of the rotation rod 249 fixedly connects to one end of the fixing part or connection part 245, and the other end of the connection part 245 fixedly connects to one plane of a slab-shape connection part 253. Further, the other plane of the slab-shape connection part 253 fixedly connects to the support desk 102.

Figure 13:
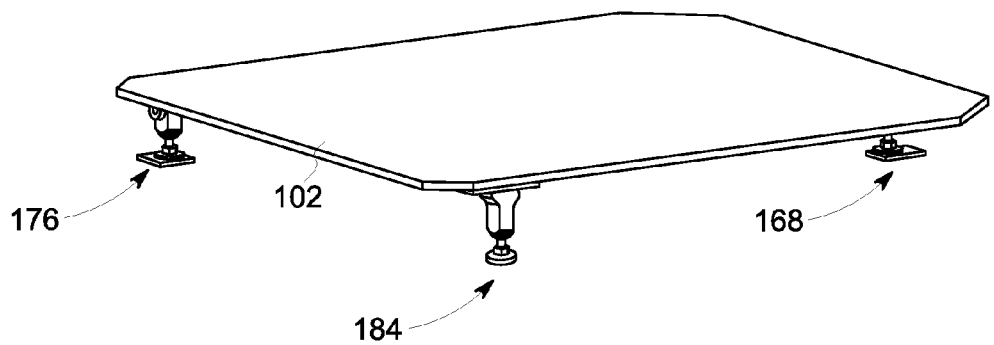
FIG. 13 shows a schematic stereogram in which multiple adjustable feet support a load bearing mechanism in a lifting device shown in FIG. 1.
Figure 14:
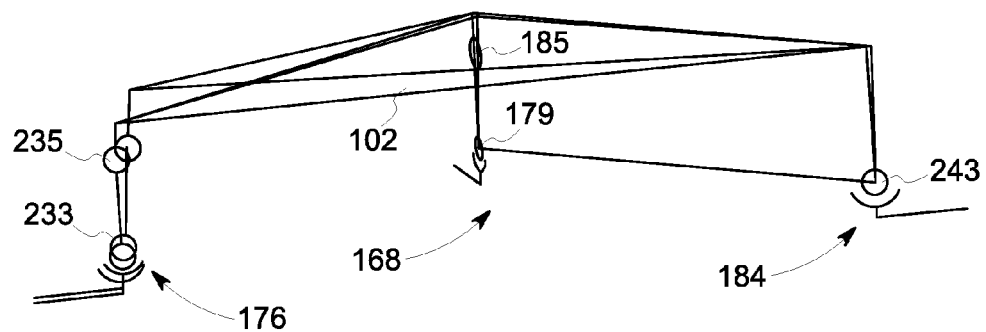
FIG. 14 shows a schematic diagram in which multiple adjustable feet automatically adjust a height of a load bearing mechanism.

FIG. 13 shows a schematic stereogram in which three adjustable feet 168, 176, and 184 support a load bearing mechanism or support desk 102. In actual operation, in some cases, the support desk 102 may not in a horizontal state when the first, second, and third lifting mechanisms 105, 107, and 109 drive the load bearing mechanism or support desk 102 to move up and down. For example, in one case, as shown in FIG. 14, a height of the support desk 102 in a location of the second adjustable foot 176 is higher than a height of a support desk 101 in a location of the first adjustable foot 168, and is also higher than a height of the support desk 102 in a location of the third adjustable foot 184. In this case, the rotation rod of the rotation part 233 of the second adjustable foot 176 rotates by a certain degree, and the first and second bearing parts of the rotation axis part 235 rotates relatively to the third bearing part to form a certain angle. Because the rotation motions of the two parts reduce a height of the second adjustable foot 176, the support desk 102 is automatically adjusted to a horizontal state. That is, deviation along the OZ direction can be eliminated.

Similarly, in another case, a height of the support desk 102 in the location of the first adjustable foot 168 is higher than a height of a support desk in a location of the second adjustable foot 176, and is also higher than a height of the support desk 102 in a location of the third adjustable foot 184. In this case, the rotation rod of the rotation part 179 of the first adjustable foot 168 rotates by a certain degree, and the first and second bearing parts of the rotation axis part 185 rotates relatively to the third bearing part to form a certain angle. Because the rotation motions of the two parts reduce a height of the first adjustable foot 168, the support desk 102 is automatically adjusted to a horizontal state.

In addition, in some cases, the first vertical motion axis 111 of the first lifting mechanism 105 may not be parallel to the third vertical motion axis 115. In this case, the rotation axis part 185 of the first adjustable foot 168 of the first lifting mechanism 105 may rotate to form a certain angle, so as to eliminate deviation in a direction of the O-Y axis.

Similarly, in some other cases, the second vertical motion axis 113 of the second lifting mechanism 107 may not be parallel to the third vertical motion axis 115 either. In this case, the rotation axis part 235 of the second adjustable foot 168 of the second lifting mechanism 107 may also rotate to form a certain angle, so as to eliminate deviation in a direction of the O-X axis.

Although the present invention is described with reference to specific implementation manners, a person skilled in the art should understand that, many modifications and variations may be made for the present invention. For example, in a lifting mechanism, in addition to converting, by using a nut screw rod transmission mechanism, a rotation motion to a linear motion to drive a loading carriage vehicle to move up and down, in another implementation manner, a gear and gear rack drive mechanism may further be used. That is, a gear is disposed to connect to a power driving mechanism, and another gear is set to connect to the loading carriage vehicle, and the gear and the gear rack mesh together. Therefore, under a function of a driving force provided by the power driving mechanism, the gear is driven to rotate, and the gear drives the gear rack to perform a linear motion, so as to implement upward and downward motions of the loading carriage vehicle. Therefore, it should be aware that, intention of the claims lies in other reasonable modifications and variations covered in a real concept and scope of the present invention.

What is claimed is:

1. A lifting device, comprising:
a plurality of lifting mechanisms;
a power driving mechanism coupled with the plurality of lifting mechanisms for providing a driving force to the plurality of lifting mechanisms, wherein the plurality of lifting mechanisms is operated in a rolling manner for moving a load bearing mechanism at least from a location of first height to a location of second height based on the driving force, wherein at least one of the plurality of lifting mechanisms comprises a guide pillar and a loading carriage vehicle rolled along the guide pillar up and down, the loading carriage vehicle comprises at least a first roller and a second roller, the guide pillar comprises a first plane and a second plane set opposite with each other, the first roller is in contact with the first plane and the second roller is in contact with the second plane and
wherein at least one of the plurality of lifting mechanisms comprises an adjustable load bearing mechanism, the adjustable load bearing mechanism is coupled with the load bearing mechanism and is for supporting the load bearing mechanism, the adjustable load bearing mechanism comprises a spindle coupled in rotate with the load bearing mechanism and a spherical joint coupled with the spindle, and the spherical joint is rotated at an angle to allow the adjustable load bearing mechanism to adjust a height of the load bearing mechanism.

2. The lifting device of claim 1, wherein a first distance is set between the first roller and the second plane, and a second distance is set between the second roller and the first plane.

3. The lifting device of claim 1 comprising a weight balance mechanism, wherein the weight balance mechanism comprises at least one weight balance piece, the at least one weight balance piece is fixed coupled with the loading carriage vehicle, and the at least one weight balance piece is for applying a fixed lifting force for at least resisting a part of a weight force of the load bearing mechanism.

4. The lifting device of claim 1, wherein at least one of the plurality of lifting mechanisms comprises a screw rod and a nut coupled with the load bearing mechanism, the screw rod is for taking the nut to move based on the driving force provided by the power driving mechanism and the load bearing mechanism is moved from the location of first height to the location of second height.

5. The lifting device of claim 4, wherein the screw rod comprises a trapezoidal screw rod.

6. The lifting device of claim 2, comprising a weight balance mechanism, wherein the weight balance mechanism comprises at least one weight balance piece, the at least one weight balance piece is fixed coupled with the loading carriage vehicle, and the at least one weight balance piece is for applying a fixed lifting force for at least resisting a part of a weight force of the load bearing mechanism.

* * * * *